(12) United States Patent
Vouillamoz (10) Patent No.: US 8,995,237 B2
(45) Date of Patent: Mar. 31, 2015

(54) FLUID INDICATOR

(75) Inventor: Lucien Vouillamoz, Môtiers (CH)

(73) Assignee: Preciflex SA, Biel/Bienne (CH)

( * ) Notice: Subject to any disclaimer, the term of this patent is extended or adjusted under 35 U.S.C. 154(b) by 128 days.

(21) Appl. No.: 13/391,386

(22) PCT Filed: Aug. 20, 2010

(86) PCT No.: PCT/IB2010/002054
§ 371 (c)(1),
(2), (4) Date: Feb. 21, 2012

(87) PCT Pub. No.: WO2011/021097
PCT Pub. Date: Feb. 24, 2011

(65) Prior Publication Data
US 2012/0147713 A1     Jun. 14, 2012

Related U.S. Application Data

(60) Provisional application No. 61/235,725, filed on Aug. 21, 2009, provisional application No. 61/349,897, filed on May 31, 2010.

(51) Int. Cl.
    *G04B 19/00*     (2006.01)
    *G01D 13/00*     (2006.01)
    *G04B 1/26*     (2006.01)
    *G04C 17/00*     (2006.01)

(52) U.S. Cl.
    CPC .............. *G04B 1/265* (2013.01); *G04C 17/00* (2013.01)
    USPC ................................ 368/76; 368/65; 368/223

(58) Field of Classification Search
USPC .................. 116/200, 264, 273, 327, DIG. 7, 116/DIG. 23; 368/65, 93–95, 76, 223
See application file for complete search history.

(56) References Cited

U.S. PATENT DOCUMENTS

| 3,486,109 | A | * | 12/1969 | Eberhardt ....................... 324/94 |
| 3,783,598 | A | | 1/1974 | Parr |
| 3,822,544 | A | * | 7/1974 | Groves ............................ 368/65 |
| 3,938,315 | A | * | 2/1976 | Von Kemenczky ............. 368/94 |
| 4,320,757 | A | * | 3/1982 | Whitney et al. ................. 604/31 |

(Continued)

FOREIGN PATENT DOCUMENTS

| DE | 42 07 122 | 9/1993 |
| GB | 501482 | 2/1939 |

(Continued)

OTHER PUBLICATIONS

English Translation of Hessabi, DE4207122.*

(Continued)

*Primary Examiner* — Amy Cohen Johnson
*Assistant Examiner* — Matthew Powell
(74) *Attorney, Agent, or Firm* — Da Vinci Partners LLC; John Moetteli (57) ABSTRACT

A visual indicator display device includes a bracelet, a transparent capillary chamber, and a displacement member. The transparent capillary chamber is matched to an indicia and has a primary length and a width less than the primary length. The displacement member is functionally disposed at one end of the capillary chamber and is responsive to a measureable input for moving a fluid contained therein a defined amount.

32 Claims, 13 Drawing Sheets

(56) References Cited

U.S. PATENT DOCUMENTS

| | | | |
|---|---|---|---|
| 4,601,707 A * | 7/1986 | Albisser et al. | 604/131 |
| 5,077,705 A * | 12/1991 | Anderson | 368/19 |
| 5,231,530 A | 7/1993 | Yen | |
| 5,249,718 A | 10/1993 | Muderlak | |
| 5,331,609 A | 7/1994 | Gubin | |
| 6,973,894 B1 * | 12/2005 | Adamy et al. | 116/206 |
| 7,245,561 B2 * | 7/2007 | Coleman | 368/65 |
| 7,505,372 B2 * | 3/2009 | Borg | 368/65 |
| 2002/0145945 A1 * | 10/2002 | Bucci | 368/223 |
| 2005/0083787 A1 * | 4/2005 | Perez et al. | 368/223 |
| 2008/0037374 A1 * | 2/2008 | Chu et al. | 368/82 |
| 2008/0130421 A1 * | 6/2008 | Akaiwa et al. | 368/82 |
| 2009/0219789 A1 * | 9/2009 | Meadows | 368/223 |

FOREIGN PATENT DOCUMENTS

| | | |
|---|---|---|
| GB | 882818 | 11/1961 |
| GB | 2 077 110 | 12/1981 |
| KR | 20030047834 | 6/2003 |
| WO | WO 82/03556 | 10/1982 |
| WO | WO 95/14497 | 6/1995 |
| WO | WO 2007/141218 | 12/2007 |

OTHER PUBLICATIONS

International Search Reports.

* cited by examiner

FLUID INDICATOR

CROSS REFERENCE TO RELATED APPLICATIONS

This application claims the benefit of U.S. Provisional Application No. 61/235,725, filed 21 Aug. 2009 and U.S. Provisional Application 61/349,897, filed 31 May 2010, the contents of which are incorporated herein by reference thereto.

COPYRIGHT & LEGAL NOTICE

A portion of the disclosure of this patent document contains material which is subject to copyright protection. The copyright owner has no objection to the facsimile reproduction by anyone of the patent document or the patent disclosure as it appears in the Patent and Trademark Office patent file or records, but otherwise reserves all copyright rights whatsoever. Further, no reference to third party patents or articles made herein is to be construed as an admission that the present invention is not entitled to antedate such material by virtue of prior invention.

BACKGROUND OF THE INVENTION

This invention relates to indicators and in particular analog visual indicators which indicate using a liquid medium.

Analog indicators have existed since time immemorial. The hour glass, for example, uses sand or water which, influenced by the weight of gravity, moves from one reservoir to another by passing through a small aperture therebetween. Another example of an ancient analog indicator is the "Clepsydra", as illustrated in "Horloges Anciennes" by Richard Miihe and Horand M. Vogel, French Edition, Office du Livre, Fribourg, 1978, page 9.

Figure 1:
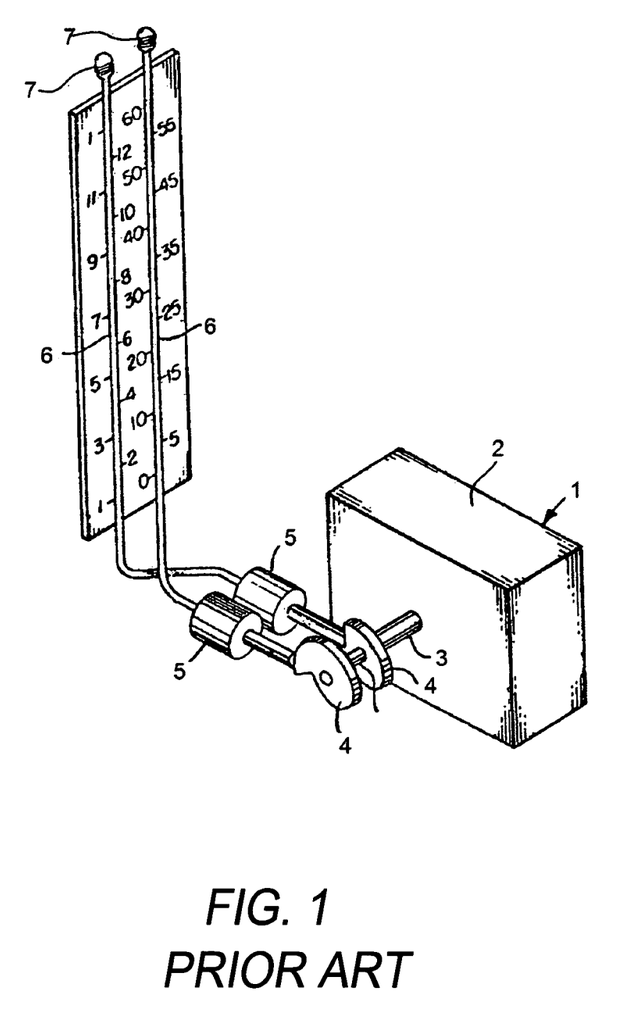
FIG. 1 is a side, cross-sectional view of an analog indicator of the prior art.
Figure 2:
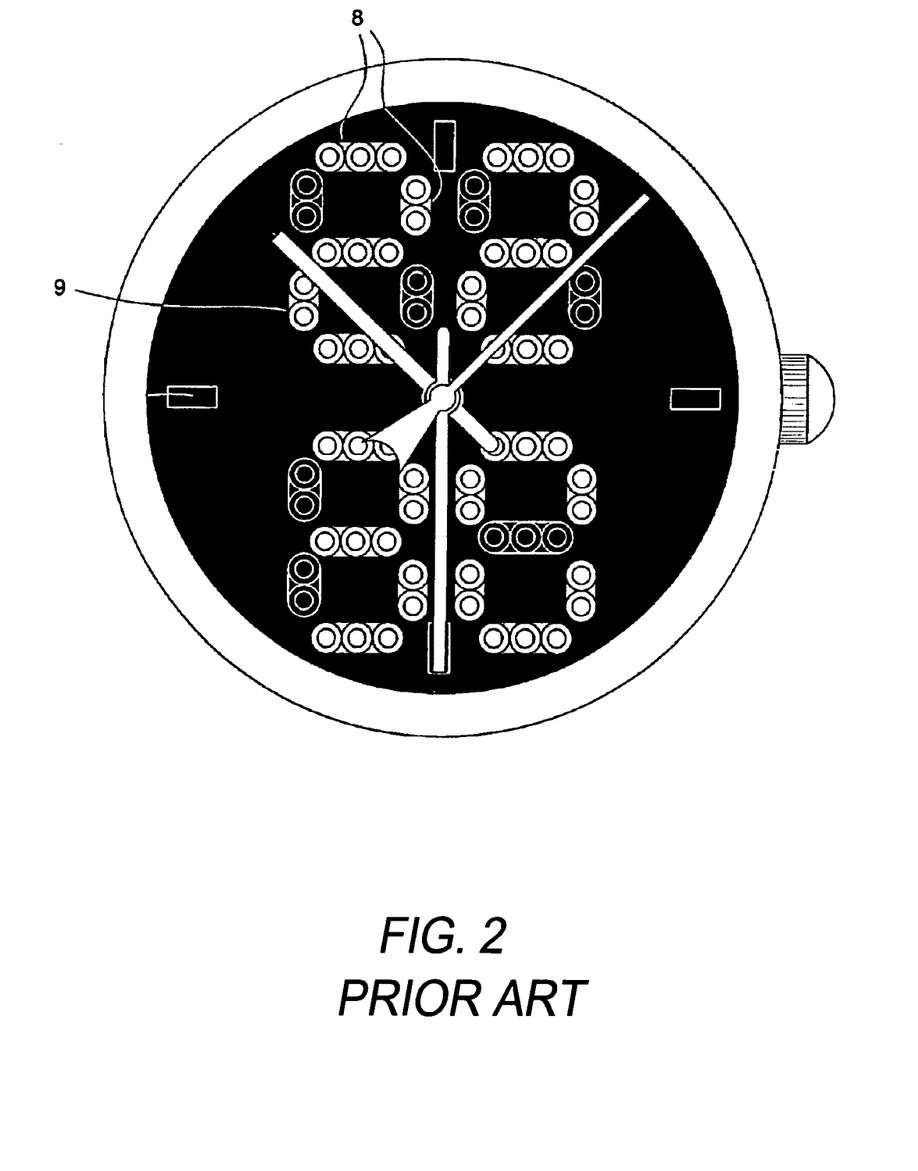
FIG. 2 is a top view of a digital indicator of the prior art.

Referring to FIG. 1, U.S. Pat. No. 3,783,598 describes an instrument 1 having a movement 2, a drive shaft 3, cams 4, pistons 5, fluid filled capillaries 6 and a relief chamber 7. Such instrument indicates time. Referring to FIG. 2, timepieces exist that use a liquid pumped into cavities 8 below which are semi-transparent stones 9, to create a digital representation of time.

These prior devices are cumbersome, requiring significant or dedicated space for indicating the value, lack accuracy or only give the impression of a fluid indicator.

What is needed is a visual indicator that provides a quickly read indication of a measured value, such as speed, temperature, instantaneous time, the time passed, or time remaining before a certain event.

SUMMARY OF THE INVENTION

A visual indicator display device includes a bracelet, a transparent capillary chamber, and a displacement member. The transparent capillary chamber is matched to an indicia and has a primary length and a width less than the primary length. The displacement member is functionally disposed at one end of the capillary chamber and is responsive to a measureable input for moving a fluid contained therein a defined amount.

An object of the invention is to provide a visual indicator which takes up minimal space on an indicator panel, whether, but not restricted to, on an automobile dashboard or integrated into a textile item.

Another object of the invention is to provide a flexible visual indicator which adapts to requirements which do not readily permit a straight, rigid indicator, such as when such indicator is worn on a wrist, ankles, a head or around or along some part of human body, or on objects such as clothes, sporting articles, vehicles, buildings, works of art or other objects susceptible to be used to show a measured value.

Another object of the invention is to provide an aesthetically and intellectually attractive indicator.

Those skilled in the art will appreciate that elements in the figures are illustrated for simplicity and clarity and have not necessarily been drawn to scale. For example, dimensions may be exaggerated relative to other elements to help improve understanding of the invention and its embodiments. Furthermore, when the terms 'first', 'second', and the like are used herein, their use is intended for distinguishing between similar elements and not necessarily for describing a sequential or chronological order. Moreover, relative terms like 'front', 'back', 'top' and 'bottom', and the like in the description and/or in the claims are not necessarily used for describing exclusive relative position. Those skilled in the art will therefore understand that such terms may be interchangeable with other terms, and that the embodiments described herein are capable of operating in other orientations than those explicitly illustrated or otherwise described.

DETAILED DESCRIPTION OF THE PREFERRED EMBODIMENT

The following description is not intended to limit the scope of the invention in any way as they are exemplary in nature and serve to describe the best mode of the invention known to the inventors as of the filing date hereof. Consequently, changes may be made in the arrangement and/or function of any of the elements described in the disclosed exemplary embodiments without departing from the spirit and scope of the invention.

A visual indicator display device includes a bracelet, a transparent capillary chamber, and a displacement member. The transparent capillary chamber is matched to an indicia and has a primary length and a width less than the primary length. The displacement member is functionally disposed at one end of the capillary chamber and is responsive to a measureable input for moving a fluid contained therein a defined amount.

In another embodiment, the visual indicator display device includes a transparent capillary chamber, an associated indicia and a displacement member. The capillary chamber has a first end for containing a first fluid and a second end for containing a second fluid immiscible with the first fluid so as to form a meniscus between the fluids which is visible through the capillary chamber. A suitable fluid may be an oil, a lotion, or a liquid such as a drug or other medication. The displacement member is attached to one end of the capillary chamber which is responsive to a measureable input for moving the fluids to displace the meniscus allowing the user to read a measurement from the indicia.

Figure 3:
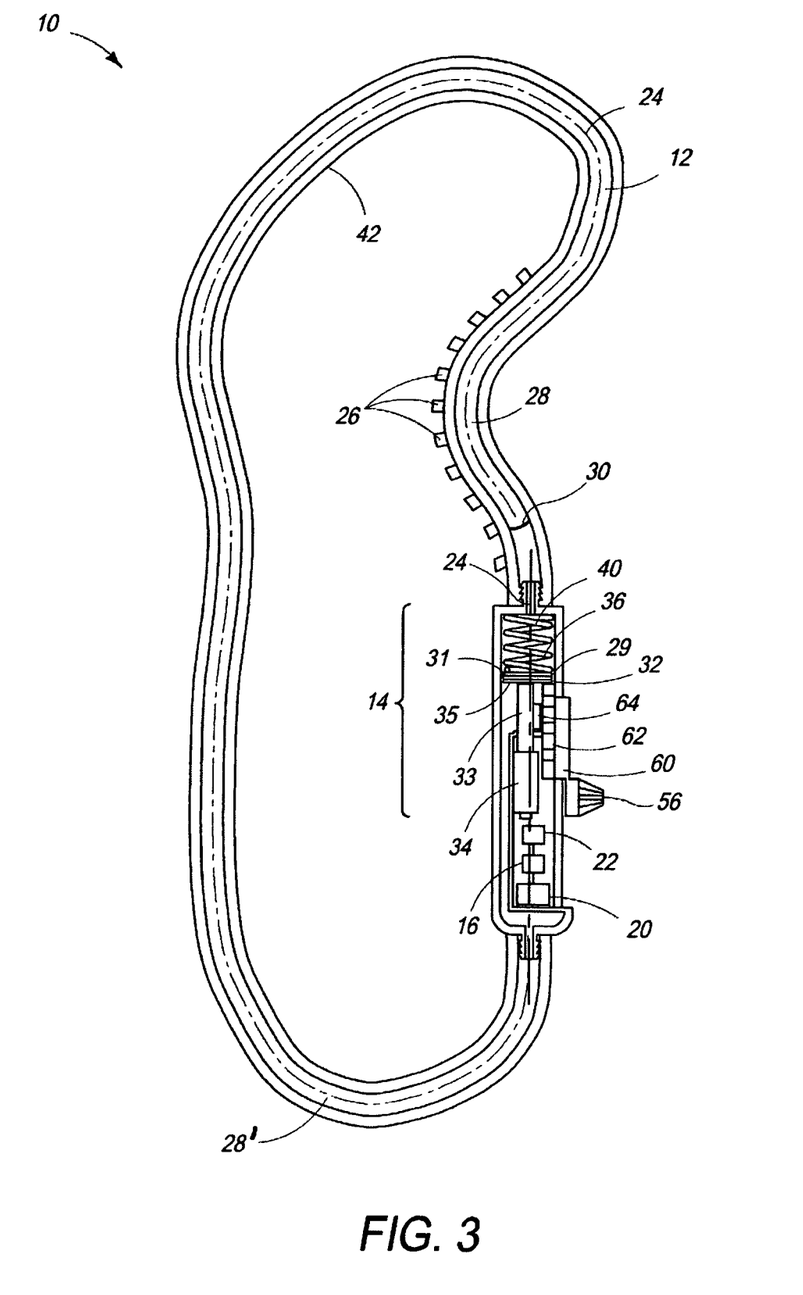
FIG. 3 is a side, cross sectional view of a first embodiment of the invention.

Referring to FIG. 3, an analog indicator 10 of the invention indicates time. The indicator 10 includes a reservoir 12, a pump 14, a measuring device 16, a feedback circuit in a controller 20 and a power supply 22'. The reservoir 12 has a longitudinal axis 24 along which a indicia or a scale device 26 is disposed and is adapted for containing a fluid 28 bounded by at least an indicator surface 30, generally the meniscus of the fluid (such may also be a surface of a plunger, floating piston, float member or barrier 27 which separates the fluids of like color). In a preferred embodiment, the pump 14 is made up of a plunger 32 mounted on a screw 33 driven by a micro motor 34. The plunger 32 generally uses an O-ring seal 29 disposed about its circumference, to seal against the fluid 28 passing between the top and bottom surface 31 and 35, respectively, of the plunger. The pump 14 pumps the fluid 28 into and out of the reservoir 12, by varying the volume of a lower reservoir 36. In a preferred embodiment, the measuring device 16 is an electronic clock which measures time and communicates a measured value of time to the feedback circuit 20. The feedback circuit 20, powered by the power supply 22, receives a measured time input from the measuring device 16 corresponding to a position on the scale device 26 and, in response thereto, activates the pump 14 to pump or move the fluid 28 from the lower reservoir 36 into the reservoir 12, until the surface 30 of the fluid reaches a desired position in relation to the corresponding position on the indicia 26. The power supply 22 powers the pump 14 and feedback circuit 20. As shown, the reservoir 12 communicates the fluid 28, or a second fluid 28' to an opposite side of the plunger 32, to act on the bottom surface 35 thereof. In this manner, pressure is equalized on each side 31 and 35 of the plunger, and a pressure relief reservoir is not required.

Further, optionally, an optical fiber and an LED light source illuminate the fluid 28 in the reservoir 12 in a known manner.

A potentiometer 56 regulates the voltage setting to a displacement control system 60. The displacement control system 60 includes an incremental position sensor 62, for example, the tracker NSE-5310 (the specification of which is attached as Appendix A to U.S. Provisional Application No. 61/235,725, filed 21 Aug. 2009, incorporated herein by reference hereto) located adjacent the plunger 32. This control system 60 includes encoding for direct digital output, in which a hall element array on the chip 62 is used to derive the incremental position of an external magnetic strip 64 placed adjacent the chip at a distance of approximately 0.3 mm (typically), the magnetic strip 64 being attached to the plunger 32 in order to translate therewith. This sensor array detects the ends of the magnetic strip to provide a zero reference point.

In an alternate embodiment, the power supply 22 can be solar cells, a wound watch spring, movement captured by an oscillating mass (such as used in automatic watches), or a pneumatic system storing compressed air.

To return the fluid 28 to an initial position, such as 6:00 AM, for example, the plunger 32 may be returned by a return spring 40 or a magnetic device (not shown). Other options are conceivable, of course, which include the return line 42, which allows simple reversing of the motor 34 to reset the indicator 10.

A suitable motor 34 is referred to by its trademark SQUIGGLE™ motor, available from New Scale Technologies, Inc. of New York, USA.

Figure 4A:
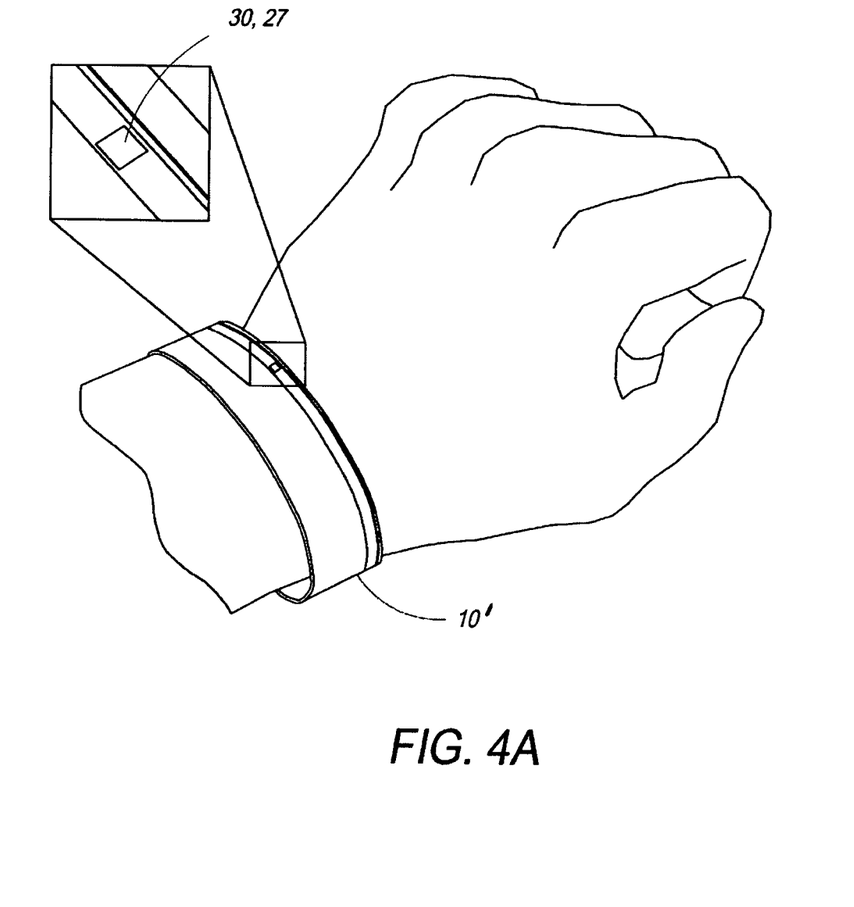
FIG. 4A is a perspective view of a second embodiment of the invention.
Figure 4B:
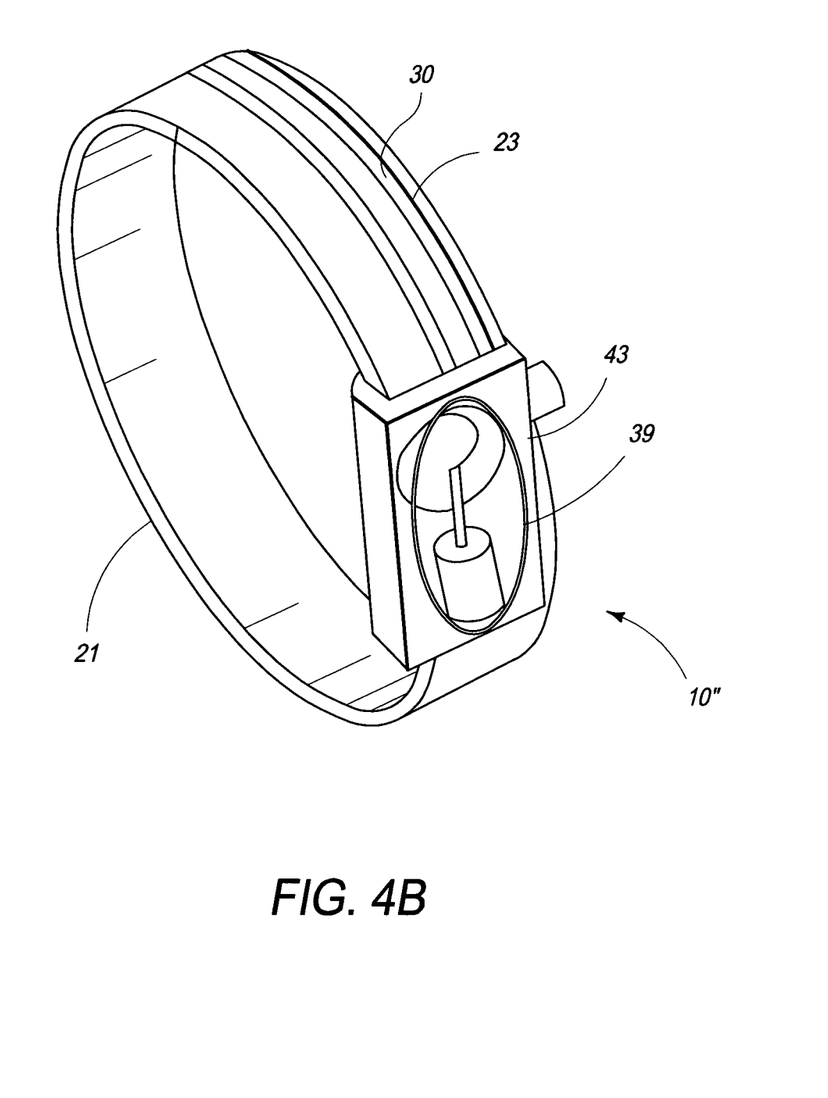
FIG. 4B is a second perspective view of the second embodiment of the invention.

Referring now to FIGS. 4A and 4B, an application of the analog indicator of the invention is a wrist watch or necklace 10 worn around the user's wrist. The reservoir 12' may be made of a transparent or translucent material, or a mixture of transparent and translucent material, formed in any desired shape. It may be made of plastic, rubber, silicon or any suitable material. An elastic material has the advantage that the bracelet 21 may be stretched over the user's wrist. In addition, the fluidic display 23 may be supplemented with a standard watch face 39 on the casing 43.

Figure 5:
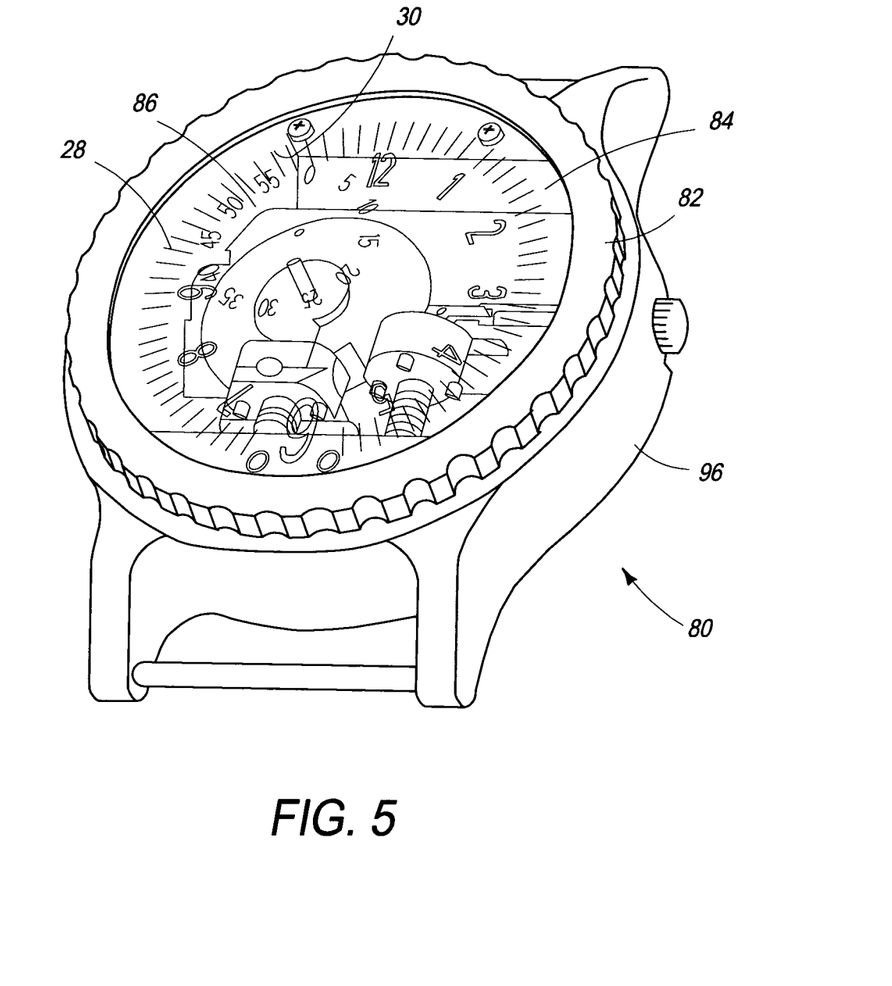
FIG. 5 is a perspective, partially transparent view of a timepiece of the invention.
Figure 6:
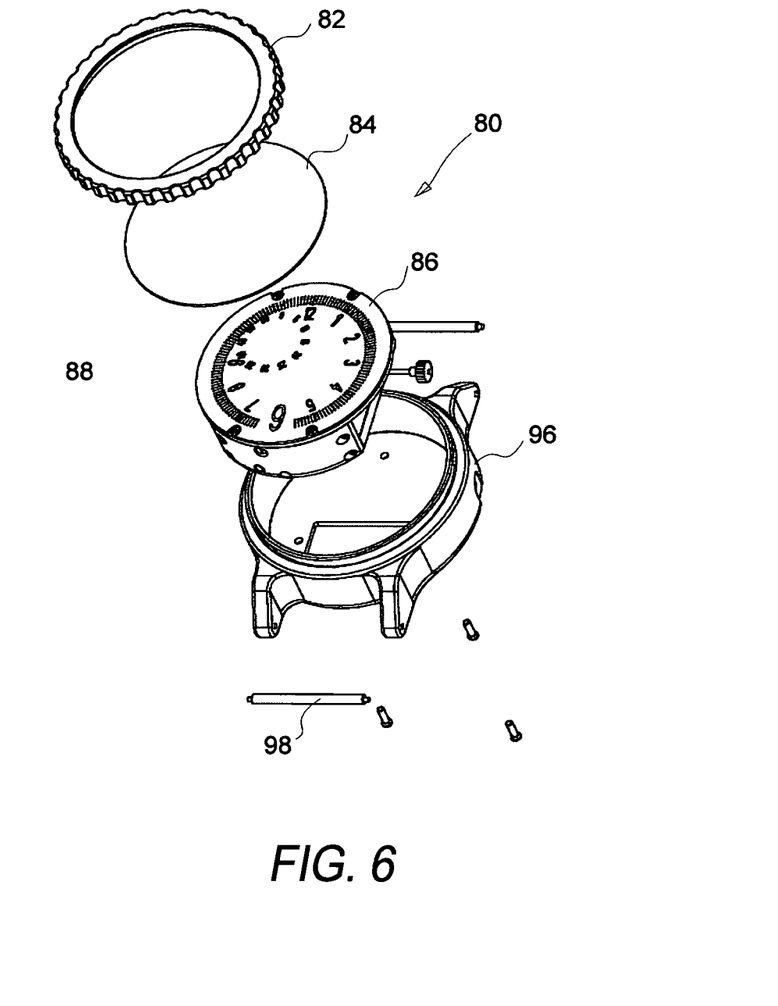
FIG. 6 is an exploded view of the timepiece of FIG. 5.

Referring now to FIGS. 5 and 6, in another embodiment, the invention is embodied in a wristwatch 80. The wristwatch 80 includes a bezel 82, a crystal 84, an at least partially transparent dial 86, a watch mechanism 88 which includes a fluid displacement device 90 (shown in FIG. 7), a capillary manifold 92 (shown in FIG. 7), a watch movement subassembly 94 (shown in FIG. 8), and a case body 96. In a known manner, the bezel 82 encapsulates the crystal 84 against the watch mechanism 88 against the case body 96, sealing the watch mechanism within an exterior housing against the elements (rain, water, snow, etc). Note that the lower part of the casing can also be transparent, to expose the inner workings of the watch to the user. A bracelet pin 98 is provided, to attach a bracelet (not shown).

Figure 7:
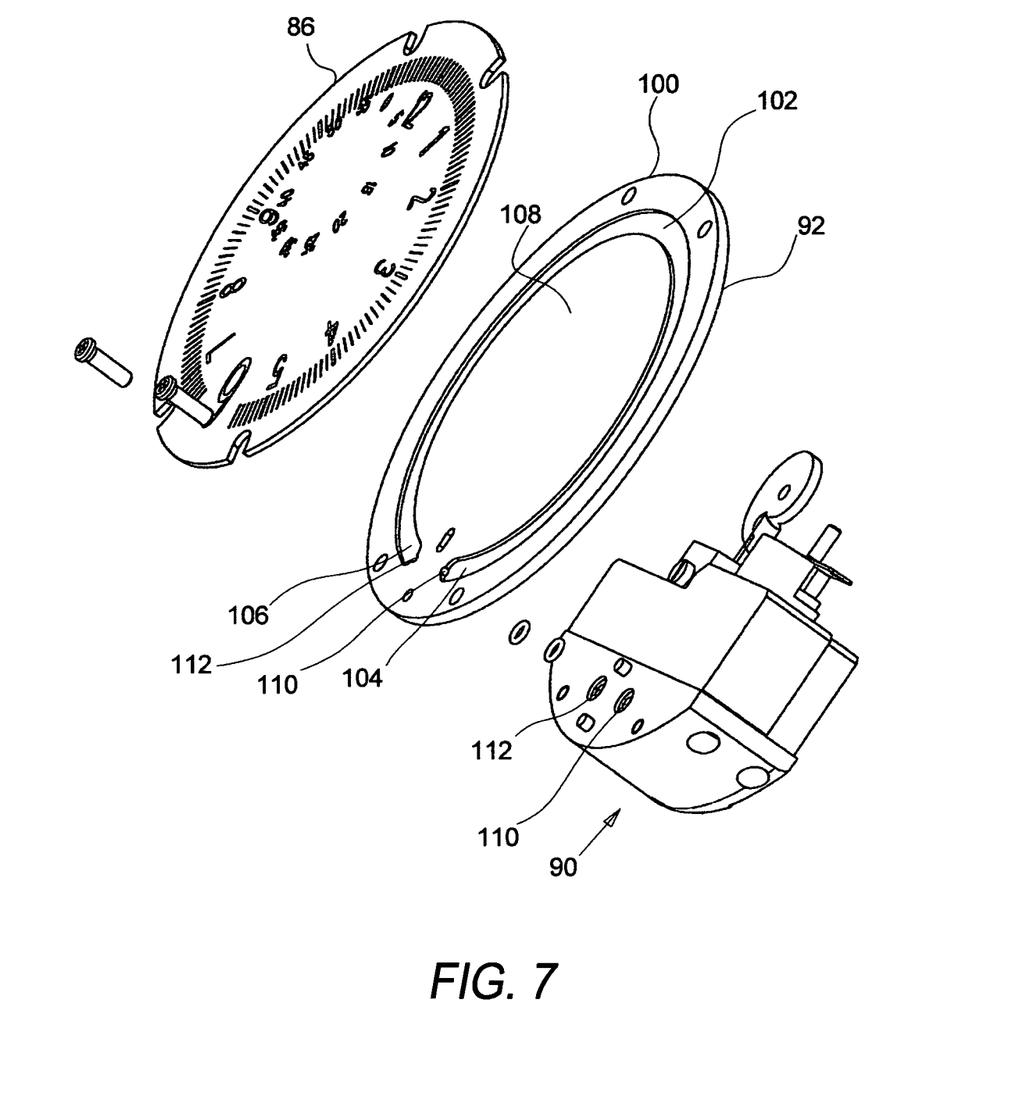
FIG. 7 is a perspective, exploded view of the face, capillary tube and fluid displacement device of the timepiece of FIG. 5.

Referring now to FIG. 7, the capillary manifold 92 of the wristwatch 80 is formed of a flat, round plate 100. A circumferential capillary channel 102 is formed in the plate 100, the channel extending proximate the external periphery about 355 degrees, at which end points 104 and 106 are located annular passages 110 and 112 which, when the dial 86 is sealingly fastened against an upper surface 108 and the fluid displacement device 90 is fastened against the lower surface thereof, enable a fluid 113 to pass therethrough from respective fluid reservoirs 114 and 116 (shown in FIG. 10). Note that the channel 102 may extend 360 degrees, provided that the end points are positioned adjacent each other (located, with one end 106 slightly raised and the other end 106 slightly lowered (or vice versa, or alternatively, located one above the other) in a spiral-like form. Of course, the capillary channel 102 may take any form, not merely circumferential, provided that time is indicated accurately. The said fluid 113 passes via channels 120 and 122 into the circumferential channel 102. The fluid reservoirs 114 and 116 are thereby in fluid communication via these passages 110 and 112 and channels 120 and 122.

Figure 8:
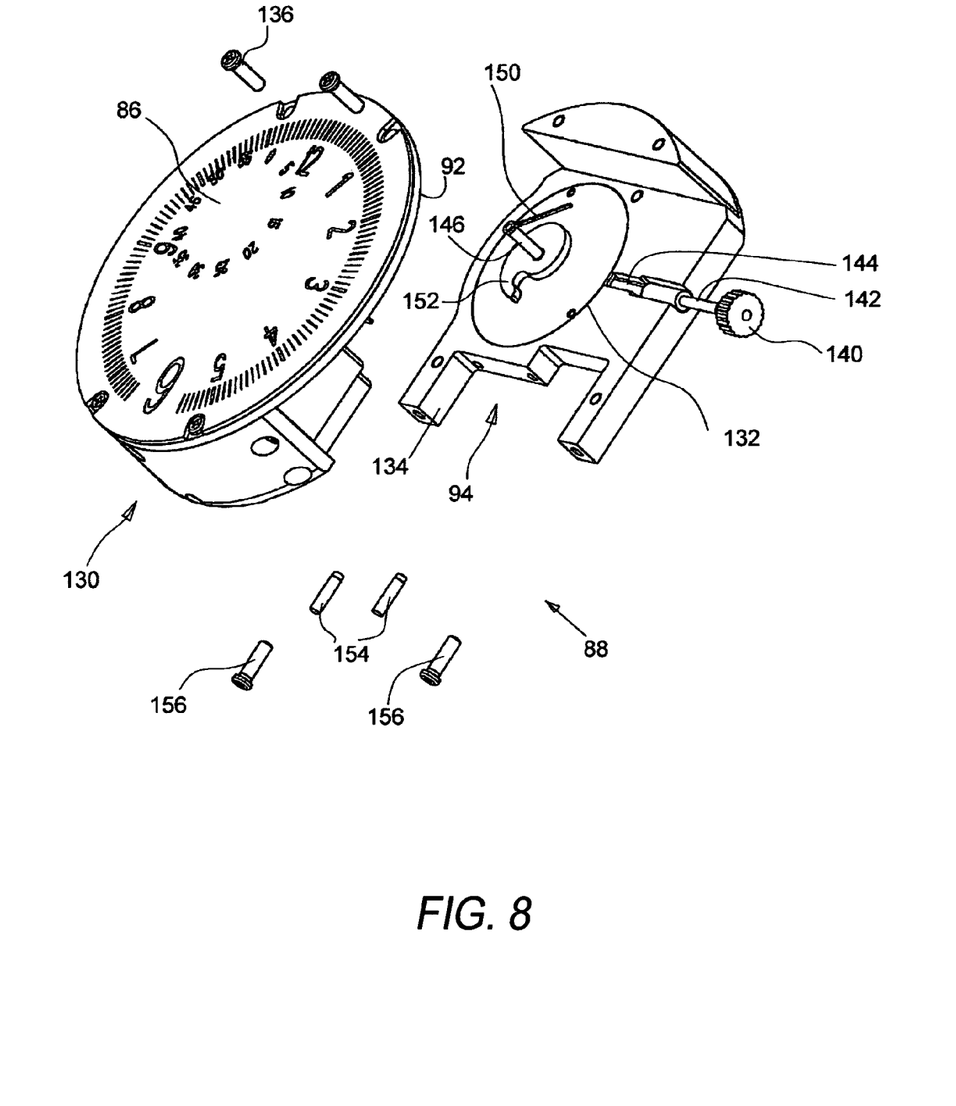
FIG. 8 is a perspective, partially exploded view of the face, capillary tube, fluid displacement device and watch movement of the invention.

Referring now to FIG. 8, the watch mechanism 88 includes a pumping subassembly 130 and a watch movement subassembly 94. The pumping subassembly 130 includes the dial 86, the capillary manifold 92 and the fluid displacement device 90 connected via screws 136. The watch movement subassembly 94 includes a watch movement 132, and a movement support 134. The watch movement 132 includes an time adjustment or crown 140 on a stem 142 around which is a stem tube 144, and an hour/second axis 146 on which is mounted a second hand 150 and a specialized cam 152. The pumping subassembly 130 and the watch movement subassembly 94 are mounted and aligned together with pins 154 and screws 156.

Figure 9:
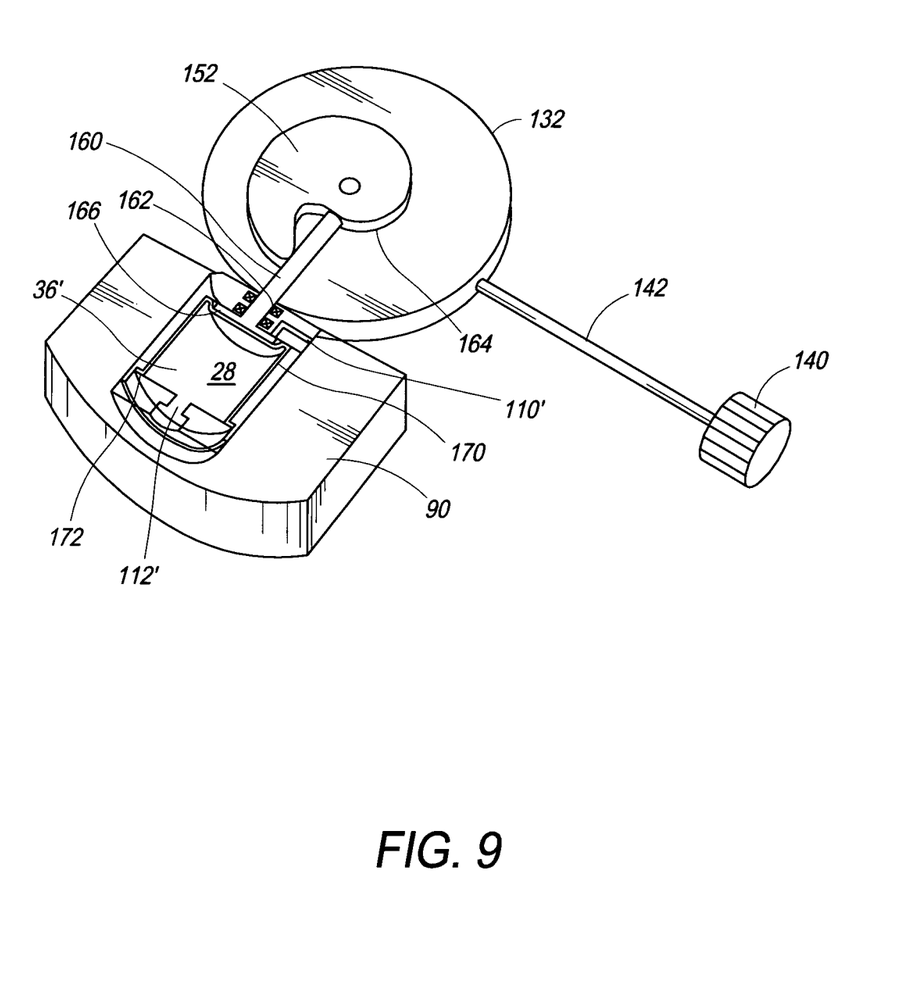
FIG. 9 is a partially disassembled view of the fluid displacement device of the invention, having one reservoir.

Referring now to FIG. 9, the cam 152 of the watch movement 132 connects to the fluid displacement device 90 via a piston shaft 160, mounted on sealed bearings 162 to axially translate, which is guided in its axial translation by a cam surface 164 thereof. The piston shaft 160 is connected to a piston head 166 which acts against a flexible rolling diaphragm 170 of a reservoir 36' (alternatively, of course the piston may have an O-ring mounted about it's periphery or otherwise be sealed, as shown in the embodiment of FIG. 3) The rolling diaphragm 170 has a flange 172 which is sealingly fixed at one end so as to effectively separate a fluid 28 from below the piston head 166, from a fluid 28' (which may include air as a fluid gas) above the piston. The reservoir 36' is shown in an extreme position. A passageway 112' leads to the capillary channel 102, and a passageway 110' provides a return passage to the opposite side of the piston head 166.

The cam 152 is formed resembling a nautilus spiral so as to progressively move the piston shaft 160 and therefore the piston head 166 to displace a determined amount of fluid 28 into the capillary channel 102, at a rate which will indicate the time accurately. Of course, a similar determined amount of drug or perfume may be administered to living organism in this manner as well Referring now to FIG. 10, an alternate fluid displacement device 90 has two reservoirs 36" and 37 wherein the reservoir 36" is in an extreme, filled position. The cam 152 of the watch movement 132 connects to the fluid displacement device 90' via a piston shaft 160, mounted to axially translate in the manner described above. The cam 152 is located so that the cam surface 164' is at its lowest radial position. The piston shaft 160 is connected to a piston head 166 which acts against a flexible rolling diaphragm 170 of a reservoir 36". The rolling diaphragm 170 has a flange 172 which is sealingly fixed at one end so as to effectively seal a fluid 28' within the reservoir 36". A passageway 120 leads to passageway 112 which leads to the capillary channel 102, and then to a passageway 110 to passageway 122, which communicates with a second reservoir 37 containing a second fluid 29'. A second piston head 166' acts against a second rolling diaphragm 170' which seals the second fluid 29' in the reservoir 37. The piston head 166' is connected to a piston shaft 160' about which a return spring 40' is disposed. A meniscus 30 divides the two fluids 28' and 29' and serves as an indicator of time as it moves in a calibrated manner through the capillary channel 102.

Figure 10:
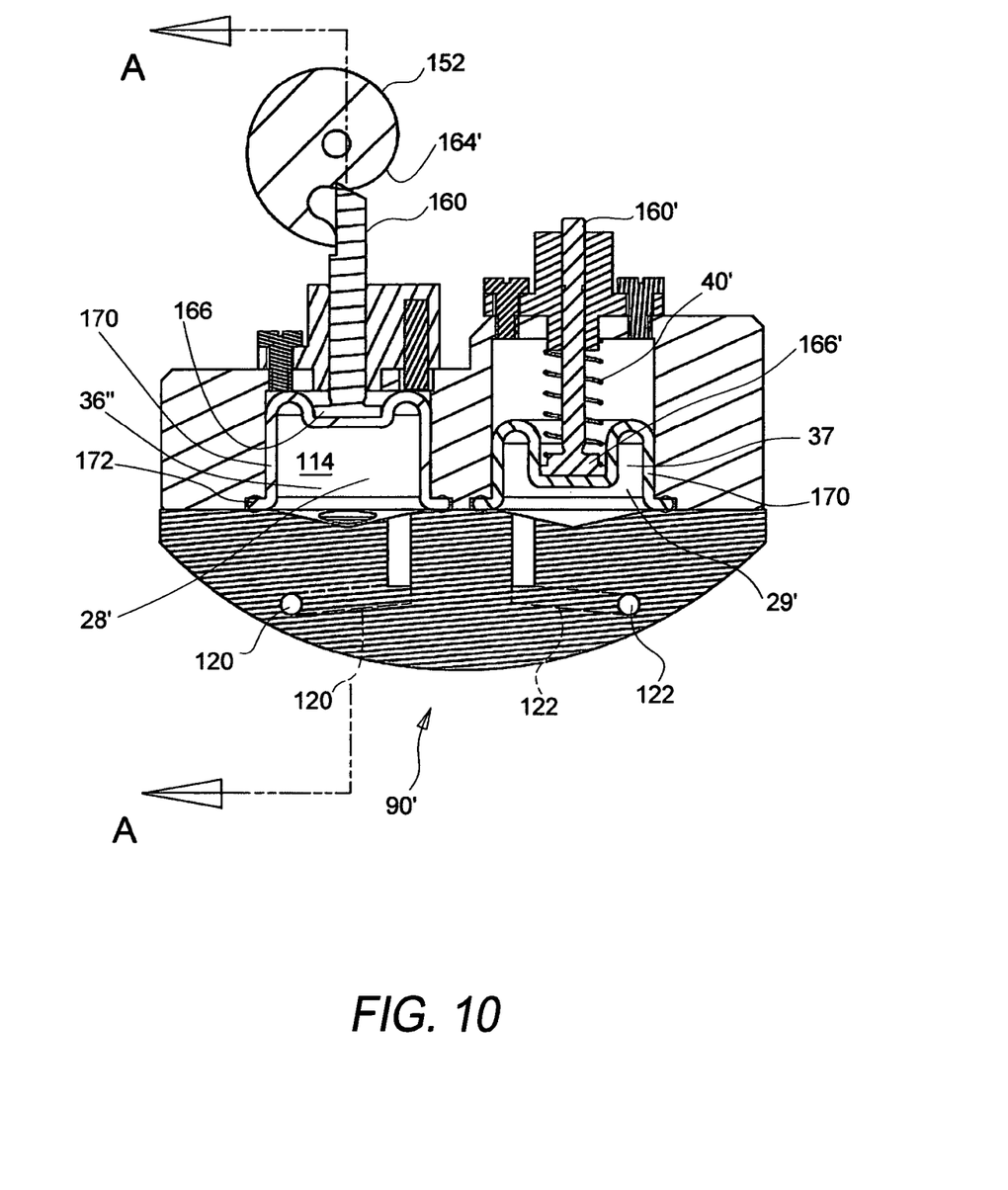
FIG. 10 is a cross-sectional view of the fluid displacement device of the invention with displacement members in a first extreme position.
Figure 11:
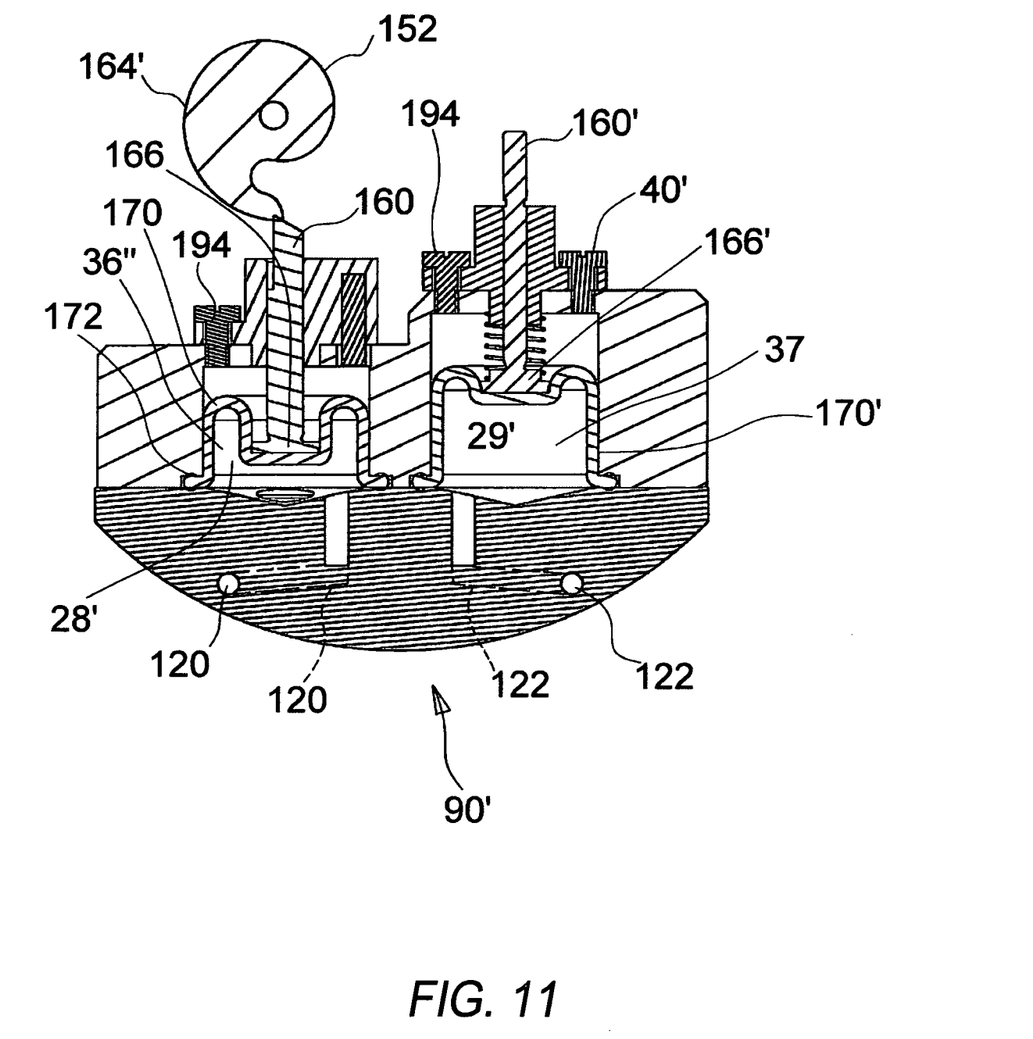
FIG. 11 is a cross-sectional view of the fluid displacement device of the invention with the displacement members in a second extreme position.

Referring now to FIG. 11, the alternate fluid displacement device 90 is shown in which the reservoir 36" is in an essentially unfilled position and in which the reservoir 37 is in a filled position. Here, the cam surface 164' is in its highest radial position with respect to the piston shaft 160'. This position would correspond to a time indication of just before 6 PM/AM. Note that the return spring 40' is in its most compressed state, so that the pressure exerted against the piston head 166' and the rolling diaphragm 170' causes the fluid 29' to be biased to return to the initial state shown in FIG. 10, after the cam 152 turns a few degrees further in a clockwise direction, thereby toggling to a position in which the cam is in the lowest radial position with respect to the piston shaft 160.

Figure 12:
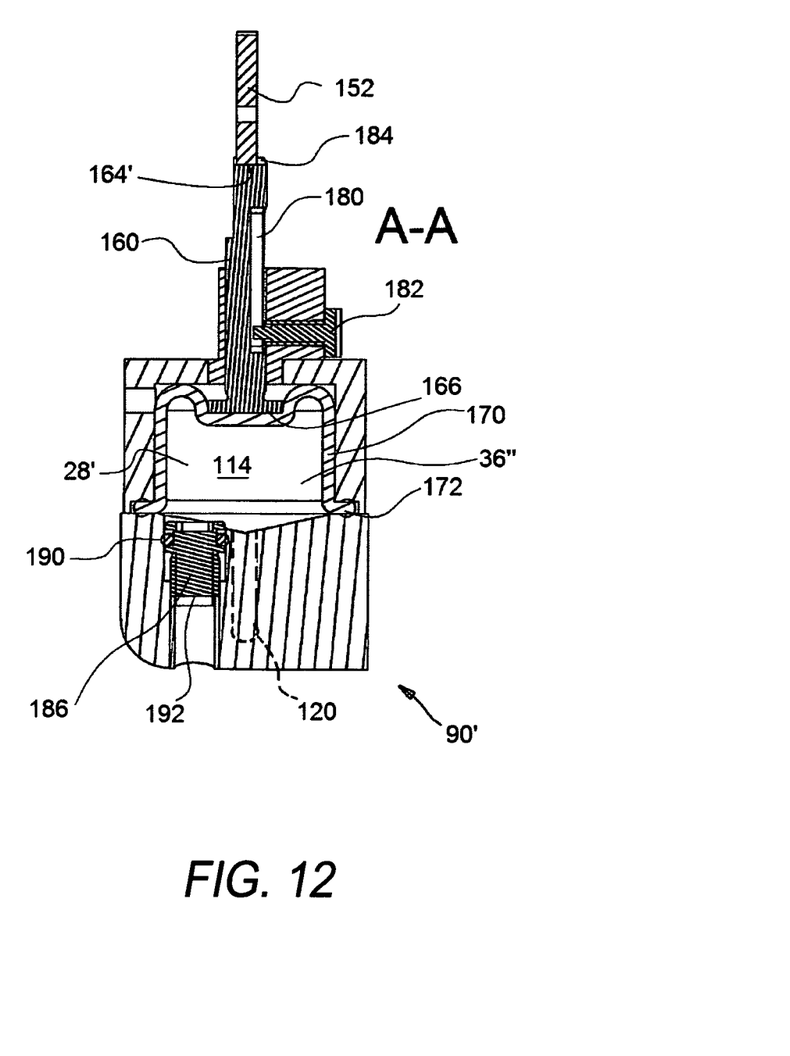
FIG. 12 is a cross-sectional view of a reservoir and displacement member of the invention, showing features which aid in initializing the invention.

Referring now to FIG. 12, again, the alternate fluid displacement device 90 is shown in which the reservoir 36" is in an essentially filled position as in FIG. 10. A keyway 180 formed on the piston shaft 160 mates with a set screw 182 which screws into the keyway via threads in the fluid display subassembly 90', in order to prevent the piston shaft from rotating on its axis, thereby better maintaining the relationship between the extreme end 184 of the piston shaft and the cam surface 164'. In addition, an adjustment screw 186 having an O-ring seal 190 mounted in a recess therein includes an "ALLEN" or "TORX" interface in an exterior end 192 thereof which allows factory adjustment of the position of the meniscus 30 for calibration purposes. A septum or access port 194 (not shown) or pair thereof, made of an elastic material, may also be used to allow removal and injection of air and fluid 28' and 29' into and out of capillary channel 102 and/or reservoirs 36" and 37.

It should be noted that the invention 10, 10', 10" may be made exclusive of all electronics (such as would typically be the case where the invention is positioned in the luxury watch market). In such embodiment, the power source 22" may be movement from an oscillating mass, which winds a watch spring, which powers a gear train, for which the rate of rotation is controlled by a pendulum-like regulator or oscillating disk (e.g., a balancier/turbion), which has a characteristic period, as known in the art.

Other embodiments are shown and described in appendices attached to the priority filings, which is incorporated herein in this written description.

It should be appreciated that the particular implementations shown and described herein are representative of the invention and its best mode and are not intended to limit the scope of the present invention in any way. Furthermore, the connecting lines shown in the various figures contained herein are intended to represent exemplary functional relationships and/or physical couplings between various elements. It should be noted that many alternative or additional functional relationships or physical connections may be present in a practical system.

Moreover, the system contemplates the use, sale and/or distribution of any goods, services or information having similar functionality described herein.

The specification and figures are to be considered in an illustrative manner, rather than a restrictive one and all modifications described herein are intended to be included within the scope of the invention claimed, even if such is not specifically claimed at the filing of the application. Accordingly, the scope of the invention should be determined by the claims appended hereto or later amended or added, and their legal equivalents rather than by merely the examples described above. For instance, steps recited in any method or process claims may be executed in any order and are not limited to the specific order presented in any claim. Further, the elements and/or components recited in any apparatus claims may be assembled or otherwise operationally configured in a variety of permutations to produce substantially the same result as the present invention. Consequently, the invention is not limited to the specific configuration recited in the claims.

Benefits, other advantages and solutions mentioned herein are not to be construed as critical, required or essential features or components of any or all the claims.

As used herein, the terms "comprises", "comprising", or any variation thereof, are intended to refer to a non-exclusive listing of elements, such that any process, method, article, composition or apparatus of the invention that comprises a list of elements does not include only those elements recited, but may also include other elements described in this specification. The use of the term "consisting" or "consisting of" or "consisting essentially of" is not intended to limit the scope of the invention to the enumerated elements named thereafter, unless otherwise indicated. Other combinations and/or modifications of the above-described elements, materials or structures used in the practice of the present invention may be varied or otherwise adapted by the skilled artisan to other design without departing from the general principles of the invention.

The patents and articles mentioned above are hereby incorporated by reference herein, unless otherwise noted, to the extent that the same are not inconsistent with this disclosure.

Other characteristics and modes of execution of the invention are described in the appended claims.

Further, the invention should be considered as comprising all possible combinations of every feature described in the instant specification, appended claims, and/or drawing figures which may be considered new, inventive and industrially applicable.

Multiple variations and modifications are possible in the embodiments of the invention described here. Although certain illustrative embodiments of the invention have been shown and described here, a wide range of modifications, changes, and substitutions is contemplated in the foregoing disclosure. For example, such indicators can be used as speed or RPM indicators in vehicles. Further, such indicators can be used to indicate body temperature or other parameters, like heart rate in sports, or in indicators used in medical devices or diagnostic equipment. While the above description contains many specifics, these should not be construed as limitations on the scope of the invention, but rather as exemplifications of one or another preferred embodiment thereof. In some instances, some features of the present invention may be employed without a corresponding use of the other features. In addition, the term "flexible" as used herein encompasses the concept of variable, in that a variable volume reservoir should be considered a flexible chamber, even if no individual components flex. Accordingly, it is appropriate that the foregoing description be construed broadly and understood as being given by way of illustration and example only, the spirit and scope of the invention being limited only by the claims which ultimately issue in this application.

What is claimed is:

1. A visual indicator display device in a timepiece comprising:
    a transparent elongated capillary chamber for containing a first and a second fluid separated by a moveable, continuous fluid boundary which substantially spans the entire interior cross-section of the capillary chamber in an uninterrupted manner, the capillary chamber having an indicator portion having a primary length and a characteristic transverse cross-section which is much smaller than the primary length and wherein the capillary chamber, along the indicator portion, is adapted to be matched to a numbered indicia for measuring a position of the boundary, wherein the chamber has a first end adapted to contain the first fluid and a second end adapted to contain the second fluid; and
    a displacement member functionally disposed at one end of the capillary chamber which is responsive to a measureable input for moving the boundary of the fluid contained therein a defined amount.

2. The visual indicator of claim 1 wherein the primary length is a circumferential length.

3. The visual indicator of claim 1 wherein the width is a radial width.

4. The visual indicator of claim 1, wherein the primary length is a spline length.

5. The visual indicator of claim 1, further comprising a bracelet and wherein the capillary chamber further comprises the bracelet, the bracelet being adapted to be worn around an appendage of a wearer and, the bracelet being flexible.

6. The visual indicator of claim 1, wherein the first and second fluid are immiscible.

7. The visual indicator of claim 6, wherein the boundary between the fluids is a meniscus.

8. The visual display of claim 6 wherein the immiscible fluids are of different colors so as to better perceive the meniscus.

9. The visual display of claim 1 wherein the displacement member is a piston located at the first end of the capillary chamber, the piston having a rear face and a front driving face to advance the fluids in the capillary chamber in a first direction.

10. The visual display of claim 9 further comprising a connective fluid pathway between the second end of the capillary chamber and the rear face of the piston wherein the rear face of the piston advances the fluids in the capillary chamber in a second direction in a closed loop manner.

11. The visual display of claim 9 further comprising a first flexible reservoir containing first fluid located between the front face of the piston and the first end of the capillary chamber, wherein the reservoir is responsive to the piston to move the fluids in the capillary chamber.

12. The visual display of claim 11 further comprising a second flexible reservoir containing second fluid, the second reservoir connected to the second end of the capillary chamber forming an open loop system for the fluids.

13. The visual display of claim 12 further comprising a spring biasing the second flexible reservoir to capture the energy created by the motion of the piston while advancing the fluids in the capillary chamber, the spring reversing the fluid flow in a second direction as the piston retreats.

14. The visual indicator display device of claim 1, wherein the visual indicator display device is adapted to be worn by a user.

15. The visual indicator display device of claim 1, wherein the numbered indicia is indicia of time.

16. A timekeeping device comprising:
    a transparent elongated capillary chamber for containing a first and a second fluid separated by a moveable continuous boundary which substantially spans the entire interior cross-section of the capillary chamber in an uninterrupted manner, the capillary chamber having an indicator portion having a primary length and a characteristic transverse cross-section which is much smaller than the primary length and wherein the capillary chamber, along the indicator portion, is adapted to be matched to a numbered indicia for measuring a position of the boundary, wherein the chamber has a first end adapted to contain the first fluid and a second end adapted to contain the second fluid; and
    a displacement member functionally disposed at one end of the capillary chamber which is responsive to a measureable input for moving the boundary a defined amount corresponding to the passing of time, thereby allowing the user to read time from the indicia.

17. The timekeeping device of claim 16 further comprising a first piston, a second piston, a first flexible reservoir, and a second reservoir, the second piston biased with a spring against the second reservoir, the spring adapted to store energy created by the expansion of the second-reservoir as the first piston displaces the first flexible reservoir causing the movement of the fluids.

18. The timekeeping device of claim 16 wherein the boundary between the fluids is a meniscus.

19. The timekeeping device of claim 16 further comprising a float member acting as the boundary between the two fluids.

20. The timekeeping device of claim 16 wherein the first and second fluid are immiscible.

21. The timekeeping device of claim 16 wherein the fluids are of different colors so as to better perceive the boundary.

22. The timekeeping device of claim 21 further comprising a watch movement for providing input to a piston.

23. The timekeeping device of claim 22 wherein the watch movement further comprises a cam output shaft driving a piston in accordance with the passage of time.

24. The timekeeping device of claim 23 further comprises a motor for driving a piston, a motor control module for the motor, and an electronic output from the movement providing input to the motor control module.

25. A timekeeping device comprising:
a transparent, elongated capillary having an indicator portion having a primary length and a characteristic transverse cross-section which is much smaller than the primary length and wherein the capillary chamber is associated with a numbered indicia, the capillary having a first end with a first flexible reservoir adapted to receive a first fluid and a second end with a second flexible reservoir adapted to contain a second fluid immiscible with the first fluid such that, when the capillary is filled with such fluids, a continuous meniscus which substantially spans the entire interior cross-section of the capillary chamber in an uninterrupted manner is formed between the fluids which meniscus is visible through the capillary;
a watch movement,
a first piston responsive to the watch movement for displacing the first flexible reservoir, a second piston biased with a spring against the second reservoir, the spring enabled to store energy created by the expansion of the second reservoir as the first piston displaces the first flexible reservoir causing the movement of the meniscus allowing the user to read time from the indicia.

26. The timekeeping device of claim 25 wherein the watch movement further comprises a cam output shaft driving the first piston in accordance with the passage of time.

27. The timekeeping device of claim 26 further comprises a motor for driving the first piston, a motor control module for the motor, and an electronic output from the movement providing input to the motor control module.

28. The timekeeping device of claim 25 wherein the immiscible fluids are of different colors so as to better perceive the meniscus.

29. A timekeeping device comprising:
a piston with a front face and a rear face,
the piston positioned within a transparent capillary having an indicator portion having a primary length and a characteristic transverse cross-section which is much smaller than the primary length and wherein the capillary chamber is associated with a numbered indicia, the capillary containing a first end in fluid communication with the front face of the piston and a second end in fluid communication with the rear face of the piston, the first end adapted for receiving a first fluid and the second adapted for receiving a second fluid immiscible with the first fluid with a continuous meniscus formed in between, wherein the meniscus substantially spans the entire interior cross-section of the capillary chamber in an uninterrupted manner; and, wherein movement of the piston displaces the meniscus allowing the user to read time from the indicia.

30. The timekeeping device of claim 29 further comprising a watch movement.

31. The timekeeping device of claim 30 further comprising a motor for driving the piston, a motor control module for the motor, and an electronic output from the movement providing input to the motor control.

32. A visual indicator display device for a wristwatch, comprising:
a bracelet adapted to be worn around an appendage of a wearer;
a transparent capillary chamber for containing a first and a second fluid separated by a boundary, the capillary chamber adapted to be matched to a numbered indicia for measuring a position of the boundary, the chamber having an indicator portion having a primary length and a characteristic width less than the primary length, wherein the chamber has a first end adapted to contain the first fluid and a second end adapted to contain the second fluid, and wherein a continuous meniscus which substantially spans the entire interior cross-section of the capillary chamber in an uninterrupted manner is formed between the fluids, the meniscus being visible through the capillary chamber; and
a displacement member functionally disposed at one end of the capillary chamber which is responsive to a measureable input for moving the boundary of the fluid contained therein a defined amount, wherein the bracelet is the capillary chamber and the capillary chamber is flexible.

* * * * *